(12) United States Patent
Sheridan et al.

(10) Patent No.: US 11,806,114 B2
(45) Date of Patent: Nov. 7, 2023

(54) MEASURING CAPILLARY REFILL TIME

(71) Applicants: ProMedix, Inc., Portland, OR (US); Welch Allyn, Inc., Skaneateles Falls, NY (US); Oregon Health & Science University, Portland, OR (US)

(72) Inventors: David Sheridan, Beaverton, OR (US); Matthew Lee Hansen, Portland, OR (US); Andrew Kibler, Lake Oswego, OR (US); Steven D. Baker, Beaverton, OR (US); Richard Allen Sunderland, Clive, IA (US); Richard H. Weitzel, Aloha, OR (US)

(73) Assignees: ProMedix, Inc., Portland, OR (US); Welch Allyn, Inc., Skaneateles Falls, NY (US); Oregon Health & Science University, Portland, OR (US)

( * ) Notice: Subject to any disclaimer, the term of this patent is extended or adjusted under 35 U.S.C. 154(b) by 383 days.

(21) Appl. No.: 16/887,846

(22) Filed: May 29, 2020

(65) Prior Publication Data
US 2021/0369124 A1 Dec. 2, 2021

(51) Int. Cl.
*A61B 5/00* (2006.01)
*A61B 5/02* (2006.01)

(52) U.S. Cl.
CPC ........ *A61B 5/02028* (2013.01); *A61B 5/6826* (2013.01); *A61B 5/6843* (2013.01);
(Continued)

(58) Field of Classification Search
CPC . A61B 5/6843; A61B 5/02028; A61B 5/0053; A61B 5/0059; A61B 5/6826;
(Continued)

(56) References Cited

U.S. PATENT DOCUMENTS

| 6,685,635 B2 * | 2/2004 | Shani ................ A61B 5/0059 600/476 |
| 2007/0282182 A1 * | 12/2007 | Messerges .......... A61B 5/6838 600/335 |

(Continued)

FOREIGN PATENT DOCUMENTS

| JP | 2012-115640 B1 | 6/2012 |
| JP | 2018-108278 A1 | 7/2018 |
| KR | 10-1459652 B1 | 11/2014 |

OTHER PUBLICATIONS

International Search Report and Written Opinion, dated Sep. 15, 2021 in PCT Patent Application No. PCTUS2134615, date of filing May 27, 2021.

*Primary Examiner* — Chu Chuan Liu
(74) *Attorney, Agent, or Firm* — Summit Patents PC (57) ABSTRACT

A system for measuring capillary refill time includes a wearable device and a control unit. The wearable device includes a force sensor to obtain a force signal and an optical sensor to obtain an optical signal. The system ensures that an applied force is acceptable in both magnitude and duration, and that a duration over which the applied force is released or removed is acceptable. These factors can establish that a capillary refill time determined or calculated therein is accurate. The system can also determine the capillary refill time based on the force and optical signals obtained by the force and optical sensors, respectively.

20 Claims, 5 Drawing Sheets

(52) U.S. Cl.
CPC ............... *A61B 2562/0219* (2013.01); *A61B 2562/0271* (2013.01)

(58) Field of Classification Search
CPC . A61B 5/1455; A61B 5/0205; A61B 5/14551; A61B 5/14552; A61B 5/021; A61B 5/02125; A61B 5/02241; A61B 5/742
See application file for complete search history.

(56) References Cited

U.S. PATENT DOCUMENTS

| | | |
|---|---|---|
| 2009/0105556 A1 | 4/2009 | Fricke |
| 2009/0143655 A1 | 6/2009 | Shani |
| 2012/0130211 A1* | 5/2012 | Kobayashi ............ A61B 5/6826 600/324 |
| 2017/0209091 A1* | 7/2017 | Weitzel ................... A61B 5/01 |

* cited by examiner

MEASURING CAPILLARY REFILL TIME

BACKGROUND

Capillary refill time (CRT) is the time taken for blood to return to an external capillary bed, such as under the fingernail, after pressure is applied to cause blanching (i.e., color loss via blood removal). CRT, regularly used or calculated by medical practitioners or caregivers, is an important indicator for various conditions including hydration, sepsis, trauma, hemorrhagic shock, and conditions affecting distal blood flow. CRT measurement can be done manually, with visual changes in color marking the blanching and refilled states.

Other devices and systems that measure CRT are overly complex in their approaches, increasing cost and reducing usability, particularly for a digit-wearable device that could be made for in-home use or as a low-cost, disposable sensor, for example used in a hospital setting. The devices and systems are deficient in regards to the inclusion of a force sensor in the digit part of the wearable device allows for linking the release of pressure or force to the CRT timing (beginning of the CRT window). This deficiency generally precludes use of manual pressure application with these devices.

What is needed is a device or system to effectively and efficiently determine capillary refill time

DETAILED DESCRIPTION

Capillary refill time (CRT), whether alone or in combination with a vital sign or another physiological signal, is an important indicator for various conditions including hydration, sepsis, trauma, hemorrhagic shock, and conditions affecting distal blood flow. The ability to accurately determine capillary refill time by medical practitioners or caregivers can be critical in properly evaluating a patient. Force application, force release, and determining a CRT start time can be crucial in accurately and properly determining CRT. Therefore, improperly or inaccurately applying force, releasing force, or determining the CRT start time can render the CRT results invalid or inaccurate.

CRT measurement can be done manually, with visual changes in color marking the blanching and refilled states, or with devices. These devices offer improvements over manual measurement and observation. These devices utilize a variety of techniques, each of which involve inducing a blanching of the patient's capillary beds, typically in a digit or extremity such as the foot, followed by optical (e.g., camera) or light-based (e.g., absorption, reflectance, or transmission) measurement of blood return to the capillary bed after pressure is released.

Some of these devices rely on an automated mechanism to apply pressure to induce the blanching period. These mechanisms include pneumatic pumps that apply pressure to the digit in an automated fashion (e.g., via a pressure cuff). Another device includes a digit sensor that is capable of manual or automated (e.g., pump) application of pressure to measure CRT using light detection. That device does not describe a mechanism to facilitate accurate timing of CRT measurement using the pressure sensor in a manual pressure application scenario. Other conventional devices include a dual wavelength finger sensor and a foot sensor, which includes a force sensor in a floor pad to trigger timing in a CRT measurement.

Various example systems, devices, and methods for determining capillary refill time are described herein. The system ensures that an applied force is acceptable in both magnitude and duration. The system also ensures that a duration over which the applied force is released or removed is acceptable. These factors can establish that a capillary refill time determined or calculated therein is accurate. Furthermore, the system can also determine that a deviation from an acceptable value or range or values, or an error in collecting or obtaining data, can require that the process be repeated to ensure that the capillary refill time is accurate. The system can be used for critical care, in-hospital sepsis prevention, dehydration management (e.g., in-home, pre-hospital, and in-hospital), the like, or combinations thereof.

A device generates an optical signal and a force signal. The optical signal is associated with light, having been emitted from an optical source, reflected from a capillary bed of a digit (e.g., a finger or a toe) and received or collected by an optical sensor. The optical signal correlates to the amount of blood flow in the distal capillary bed (e.g., more light reflected indicates less blood flow to the distal capillary bed; less light reflected indicates more blood flow to the distal capillary bed). A characteristic of the optical signal can be amplitude.

The force signal is associated with force, which is determined by a force sensor, applied to or exerted on the digit on or along a desired direction. A characteristic of the force signal can be amplitude.

The sensors convert the received stimulus (e.g., light or force) into an electrical signal (e.g., output current, output voltage, change of resistance, output current with internal gain, or the like).

The values of the optical signal vary over time due to fluctuations or changes in the light reflected through the digit. The values of the force signal vary over time due to fluctuations or changes in the force applied to or exerted on the digit. When viewed in combination, the optical and force signals can indicate critical points or elements for CRT data analysis, can provide data for CRT analysis or calculation, or both. For example, CRT is calculated as the time from force release to the time where the optical signal returns to a baseline value or within a predetermined range or percentage of the optical signal baseline. The duration over which the force decreases (i.e., force is released) and the reflected light decreases (i.e., distal capillary bed is refilled) can be used to calculate CRT.

Analysis of the signals can be used to calculate CRT. Quality metric data can be used to determine whether the data has been accurately collected or whether the CRT measurement should be repeated.

The device provides a mechanism that permits release or removal of the applied pressure over an acceptable time period. In other words, the device can determine whether or not a force release duration is within a predetermined range.

The device is suitable for measuring CRT when placed on a digit of a patient, such as a finger or toe. The device uses light detection (e.g., changes in amount of light reflection through the digit) to measure CRT with a baseline value of light reflection (i.e., light reflection through the patient's digit without application of a force) being changed via manual application of force to the digit to establish a plateau value, followed by a release of the force within an acceptable time period.

One or more algorithms that utilize CRT data, whether alone or in combination, can be implemented to determine CRT, determine one or more patient conditions associated with the CRT, or one or more treatments for the one or more conditions. The CRT data, having been collected by a CRT system, can be stored in and retrieved from the CRT system, an electronic medical record (EMR), a storage device (e.g., a hard drive or a server), or the like. The one or more conditions can be, for example, dehydration, sepsis, trauma and conditions that affect distal blood flow.

An output of the CRT system can be value, can be a qualifier (e.g., "good reading," "reading is accepted," "bad reading," "retry reading," "re-measure," or the like), can be a determination (e.g., "CRT is in an acceptable range," "Check other vital signs," or the like), the like, or combinations or multiples thereof. For example, the output can be "Reading is good. CRT is 1.82 seconds." As another example, the output can be "Re-measure. Force release was improper."

When the output is a value, the practitioner or caregiver can incorporate the value with knowledge, other empirical or clinical data, or combinations thereof to discern or diagnose the condition of the patient. For example, if the CRT is less than 2 seconds, then the operator or practitioner can conclude that the patient has or does not have one or more medical conditions (e.g., is properly hydrated or does not have sepsis). As another example, if the CRT is 2 seconds or more, then the operator or practitioner can conclude that the patient has or does not have one or more medical conditions (e.g., is not properly hydrated or has sepsis). As yet another example, if the CRT is less than 2 seconds, then the operator or practitioner can incorporate that into the patient's other data, including vital signs, other symptoms, or the like, so the operator or practitioner can determine the diagnosis or treatment.

The CRT system can also include an application, such as software or a set of firmware instructions that are implemented on a smartphone, a tablet, or a hospital monitor. The application can be configured to relay instructions, outputs feedback associated with obtaining CRT measurements, displays CRT data, provides an explanation or summary of the CRT data, the like, or combinations or multiples thereof. In one example, the application provides instructions for obtaining CRT, including real-time feedback. The application provides instructions and feedback data to the practitioner for obtaining CRT measurements. The application can communicate data for confirming a baseline or resting measurement, applying an appropriate amount of force, establishment of a plateau (blanching stabilization), determining a duration of release of force, the like, or combinations or multiples thereof. The application can also correlate or determine data associated with the CRT data capture, output CRT measurement, and conclusions drawn therefrom, including clinical estimations, measurement validation and quality metrics, or corrective instructions for CRT measurement repeat.

Figure 1A:
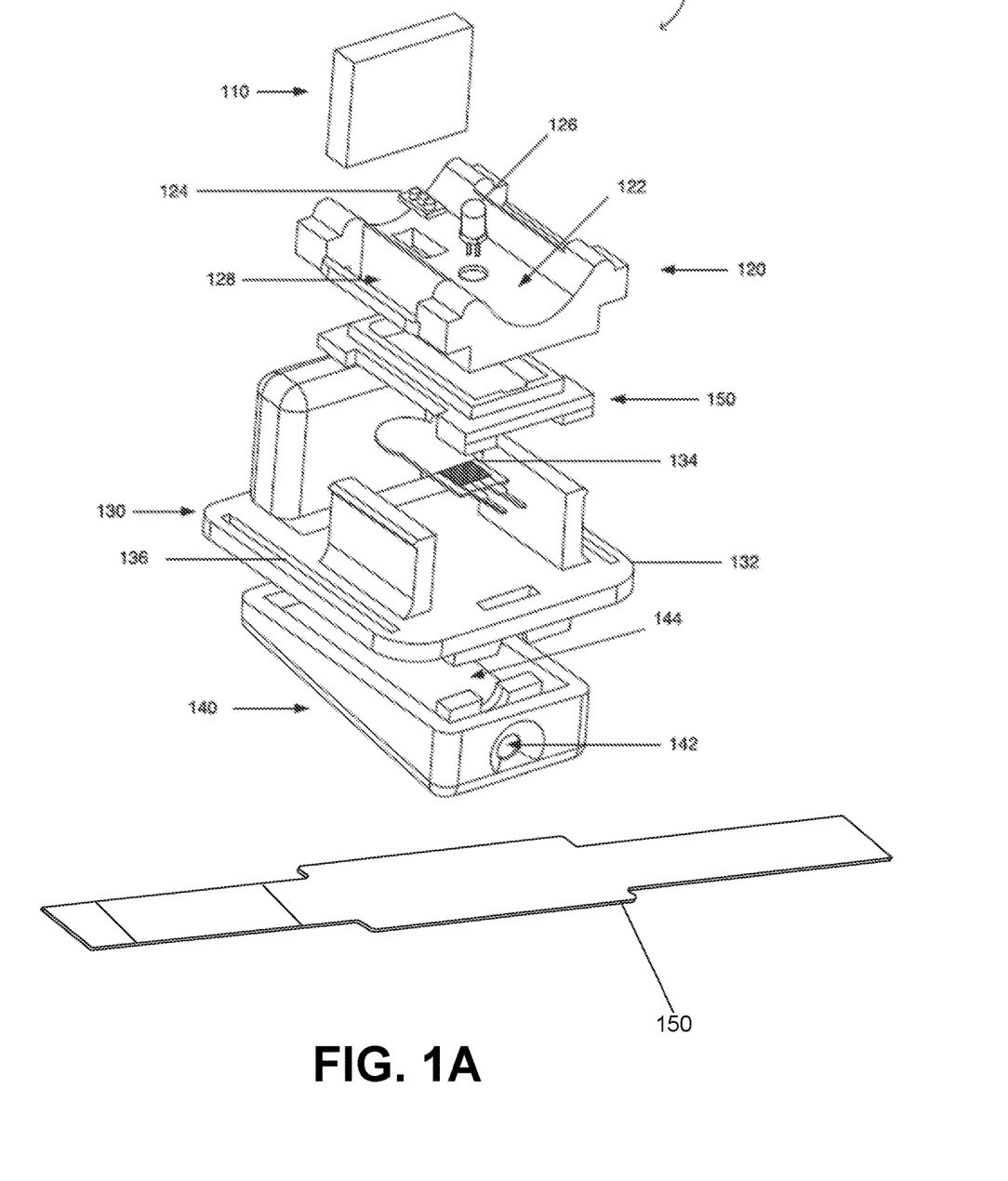
FIG. 1A is an exploded view of an example device.
Figure 1B:
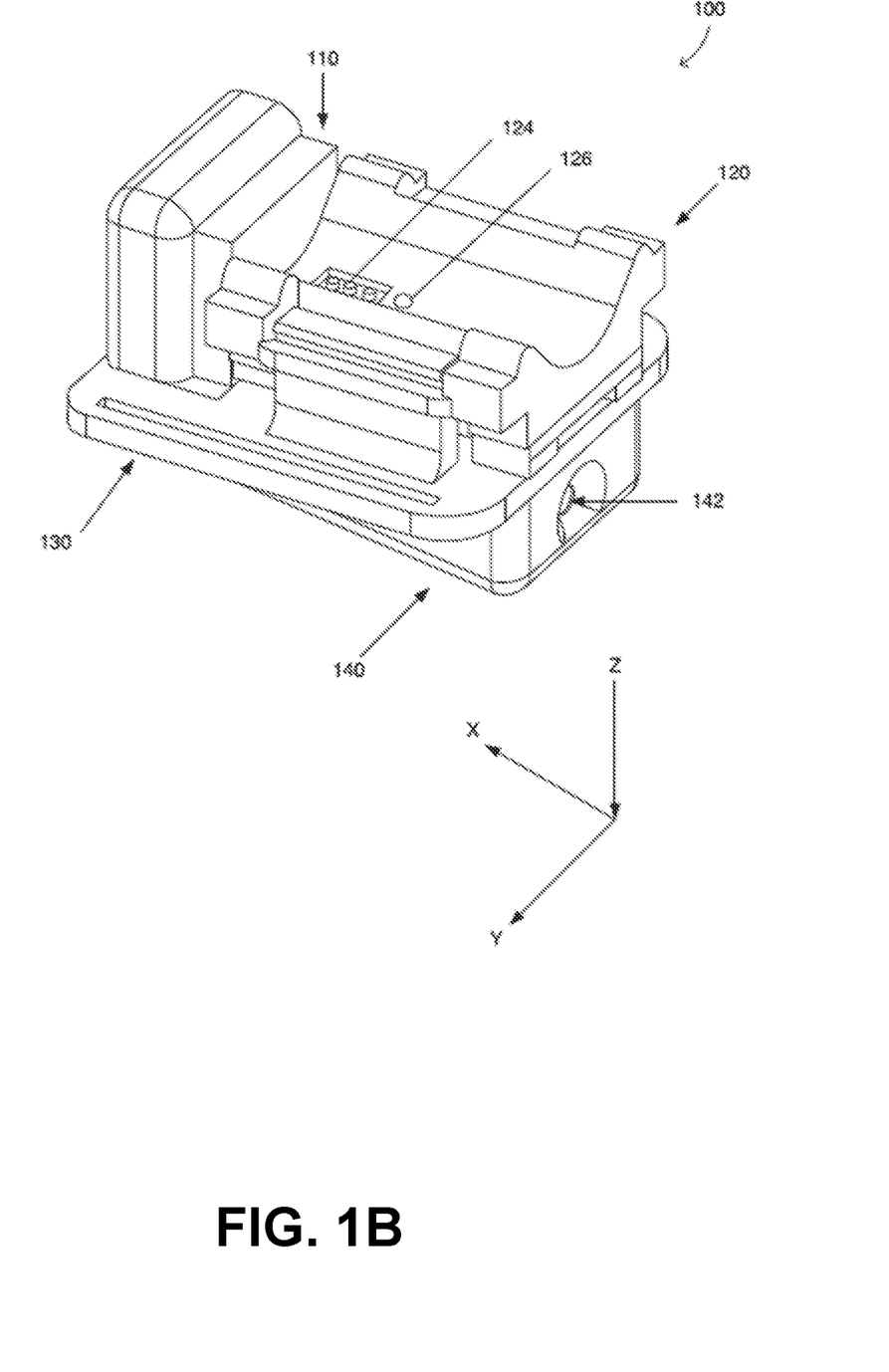
FIG. 1B is an isometric view of the example device.

FIG. 1A shows an exploded view of a device 100. FIG. 1B shows an isometric view of the device 100 having been assembled. The device 100 includes a digit plate 120, a base 130, and a connector 140. In the example shown in FIGS. 1A-1B, the device 100 can be worn in a free-form fashion (i.e., the device 100 does not need to be secured in or to a location, such as a table top). In another example, the device 100 can be a fixed, non-wearable device. The device 100 can be fixed to a table top.

The digit plate 120 includes a digit groove 122 to receive, accept, or support a digit (e.g., a toe or finger) of a patient. The digit groove 122 is concave. Alignment of the digit against, near, or proximal to an optical sensor 124 can affect testing and accurate data collection. Therefore, the digit groove 122 is sized and shaped to allow for accurate testing within a range of ages having varying digit sizes (e.g., the finger groove 122 of a first device is sized and shaped for babies, toddlers, and children ranging from 6 months to 10 years of age; the finger groove 122 of a second device is sized and shaped for children, teenagers, and adults older than 10 years of age). In one example, a diameter at an apex of the concavity of the digit groove 122 can be 8-18 mm, including, 10-16 mm, and 10 mm. An angle of a side wall of the digit groove 122 can be 20-70 degrees from a vertical axis, including 30-60 degrees, and 45 degrees. The digit groove 122 can have 0.1-2 mm of unevenness to prevent slippage of the digit within the digit groove 122.

The device 100 also includes a backstop 110. The backstop 110 includes a dent to accept a tip of the digit being received or supported by the digit groove 122, thereby aiding in digit alignment. The dent of the backstop 110 can be 0.1-10 mm, including 1-5 mm. The dent can located in the center of the backstop 110 or can be offset from the center. The backstop 110 can be composed of a polymer or an elastic or flexible material, including, without limitation, rubber, silicon rubber, urethane resin, plastic resin, the like, or combinations or multiples thereof.

The digit plate 120 also includes the optical sensor 124 to obtain an optical signal, thereby allowing for collection of baseline or resting data, blanching data, and capillary refill data based on the reflection light through the digit.

The baseline or resting data is a value or range of values used as a fixed point of reference. The baseline or resting data can be calculated by sampling variations (i.e., changes or fluctuations in reflected light) in the optical signal over time. For example, the baseline or resting data can be calculated via a sliding window, whereby a window, having a width of a set length of time, evaluates a first set of data falling within the window, and the window is then slid to a second set of data.

Blanching is when blood flow to the distal capillary bed is reduced, thereby resulting in whitish color. Blanching is calculated by determining a stable optical signal (i.e., no fluctuation or fluctuation within a given window) when a force, applied to or exerted on the digit, exceeds a threshold and maintains stability.

Capillary refill is the time it takes for blood flow to return to the distal capillary bed after blanching. Capillary refill time is calculated from the end of the blanching period to the time the optical signal returns to the baseline or resting value.

The optical sensor 124 can be a photodiode, a photovoltaic, a photoconductive device, a phototransistor, or the like. The optical sensor 124 can be embedded in the digit groove 122, can be located in a strap 150, can be located between the digit groove 122 and the digit when rested on the digit groove 122, or can be located between the digit groove 122 and the base plate 132 with an aperture (not shown) extending through the digit groove 122 to permit the passage of light. The strap 150 is not included in FIG. 1B so as to not obscure any other elements or components of the device 100.

In one example, the device 100 can also include a light source 126 to provide illumination of the patient's digit and allow for the determination of light reflection (or transmission or absorption) through the digit. The light source 126 can be at least one light emitting element (e.g., a light emitting diode, a green LED, a red LED, the like, or combinations or multiples thereof). The light source 126 can be embedded in the digit groove 122, can be located in a strap 150, can be located between the digit groove 126 and the digit when rested on the digit groove 122, or can be located between the digit groove 122 and the base plate 132 with an aperture (not shown) extending through the digit groove 122 to permit the passage of light.

In another example not shown in FIG. 1, the light source 126 is external to the device. The external light source is a light source outside of the structure or any component of the device 100. The external light source can be a lamp, a flashlight, a penlight, or any appropriate apparatus or instrument for emitting light.

When the light source 126 is external to the device 100 or included in the strap 150, the light emitted from the light source passes through the digit and is received by the optical sensor 124. Alternatively, when the light source 126 is proximal to the digit groove 122 (e.g., embedded within the digit groove 122, located between the digit and the digit groove 122, located between the digit groove 122 and the base plate 132, or the like), the light emitted by the light source 126 at least partially passes through the distal capillary bed. The light is then reflected back to the optical sensor 124. The light can be reflected back by the strap 150 or a portion of the digit (e.g., fingernail, toe nail, skin, muscle, fat, blood vessel, the like, or combinations thereof).

The amount of light reflected from the digit correlates to the amount of blood volume in the distal capillary bed (e.g., more light reflected indicates less blood flow to the distal capillary bed; less light reflected indicates more blood flow to the distal capillary bed). The optical sensor 124 converts the received light into an electrical signal (e.g., output current, output voltage, change of resistance, output current with internal gain, or the like). Additionally, the more light received, the greater the electrical signal generated by the optical sensor 124, and the less light received, the smaller the electrical signal generated by the optical sensor 124.

The digit plate 120 can also include one or more digit plate strap loops 128 to permit a strap 150 or portion thereof to pass through. In one example, the digit plate 120 includes two base plate strap loops 128, each base plate strap loop 136 on opposing sides of the digit plate 120.

The base 130 includes a base plate 132 to support a force sensor 134 and to allow for a physical connection to the connector 140. The force sensor 134 can obtain a force signal and measure force applied to or exerted on the digit within the digit groove 122 on or along a desired direction. In other words, the force sensor 134 can measure force applied along a Z-axis. One or more additional force sensors (not shown) can be included to measure forces tangential to the desired direction. In other words, the additional force sensors (not shown) can measure force applied along an X-axis, a Y-axis, or both. The additional force sensors (not shown) can conduct signal checking and error checking (e.g., provide an error status when force in a direction other than along the Z-axis exceeds a threshold amount to indicate that the applied force is not in the correct direction). The force signal can be used to determine applied force for the duration of CRT, which can further permit the timing of pressure release (e.g., manual) to correspond to CRT initiation.

The force signal can also be used to determine signal quality measurements. Signal quality measurement data can be used to determine whether the force signal has been accurately collected or whether the CRT measurement should be repeated. For example, a force signal having too much fluctuation or variation, even if properly obtained, can render the collected data inaccurate or invalid.

The base plate 130 can also include one or more base plate strap loops 136 to permit a strap 150 or portion thereof to pass through. In one example, the base plate 130 includes two base plate strap loops 136, each base plate strap loop 136 on opposing sides of the base plate 130.

The strap 150 is sized to fit a digit of a predetermined size of patients. The strap 150 can be flexible, elastic, hook and loop fastener, the like, or combinations thereof. The strap 150 can be a single piece or multiple pieces. The strap 150 can form a side of the digit plate 120 opposite the digit groove 122. The materials of the strap 150 can block ambient light to increase or enhance the accuracy of light detection via the optical sensor 124.

In one example, the strap 150 is fixedly attached to connector 140 with one or more ends fitting through the base plate strap loops 136 and the digit plate strap loops 128. In another example, the strap 150 includes a terminal end fixed attached to one of the base plate strap loops 128 with a free end capable of passing through the opposing base plate strap loop 136 and the digit plate strap loops. In yet another example, the strap 150 is not attached to the device except for when the strap 150 is inserted through the base plate strap loops 136 and digit plate strap loops 128 to secure the device 100 to the digit of the patient. Though the strap 150 is discussed herein as an attachment apparatus, another attachment apparatus can be used to attach or hold the device 100, including the force sensor 134 and the optical sensor 124, to the digit of the patient.

The connector 140 includes a hole 142 and a cavity 144. The cavity 144 can include processing circuitry, modules, or both to process data signals, communicate with a secondary device, or the like. The hole 142 is sized and shaped to permit a wire or cable to connect the processing circuitry or modules of the device 100 to a second device (e.g., an intermediary device, a control unit, the like, or combinations or multiples thereof).

For example, the device 100 can communicate sensed data (e.g., force, light, and temperature) or processed data (e.g., CRT data) directly to a control unit (not shown) via an interface or output element (e.g., LED(s) or communication module) or indirectly to the control unit (not shown) via a wired or wireless coupling to another device (not shown), such as a wrist-worn module, a smartphone or tablet, or a hospital monitor.

The construction of the device 100, including length (e.g. less than or equal to 12 inches including an intermediary device), weight (e.g., less than or equal to 5 ounces, including 0.37 ounces), and attachment to the digit, can reduce or eliminate one or more motion artifacts present in the optical signal, force signal, or both during CRT data acquisition.

Figure 2:
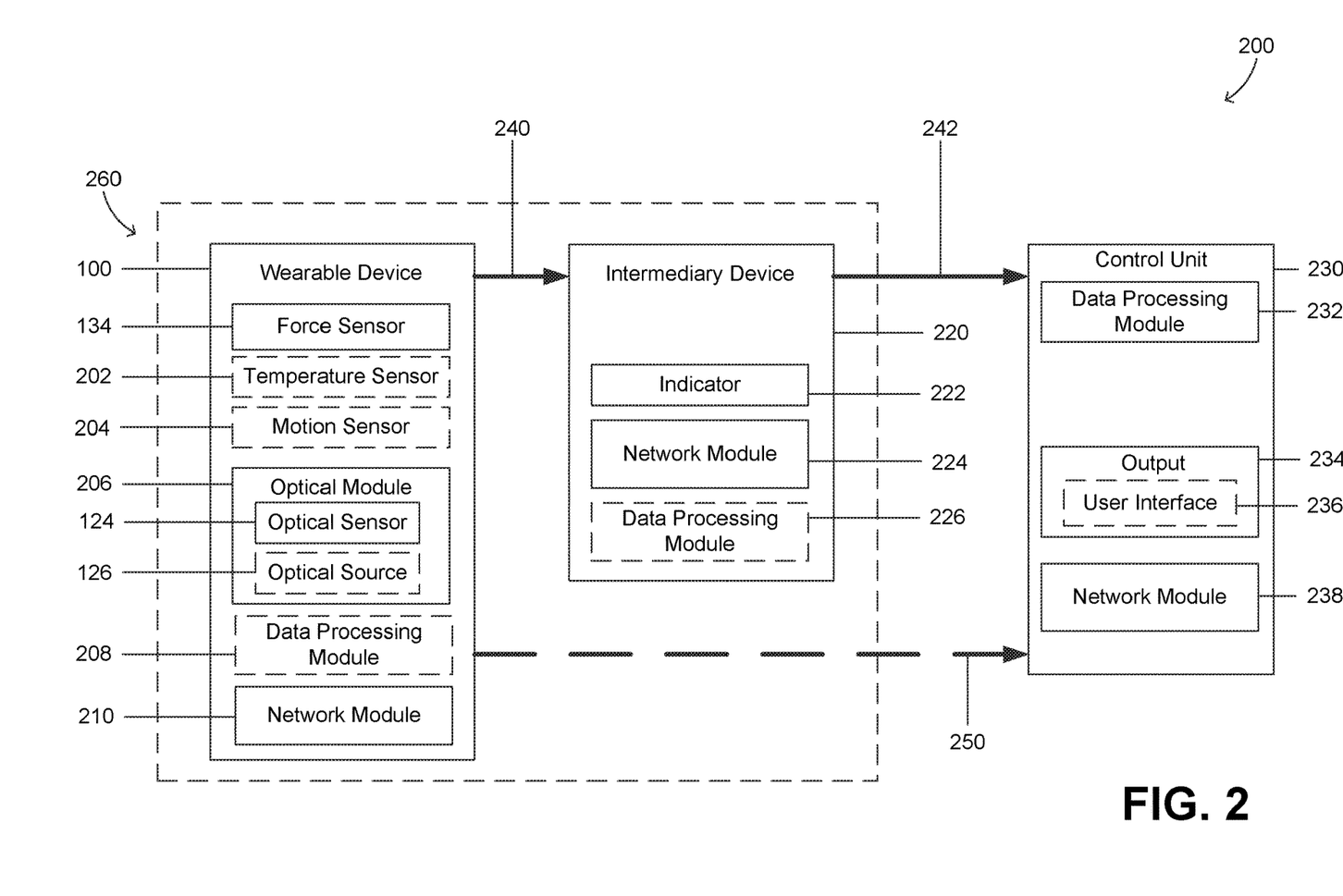
FIG. 2 is a block diagram of an example system.

FIG. 2 shows a block diagram of a CRT system 200. The CRT system 200 includes the device 100 and a control unit 230. The CRT system 200 can also include an intermediary device 220.

The device 100 includes the force sensor 134, as discussed above, and an optical module 206, which includes the optical sensor 124 and the optical source 126, as discussed above. The device 100 can also include temperature sensor 202 to determine temperature data of the patient. Because temperature can affect CRT, the temperature data can optionally be used in combination with the optical and force data to provide CRT or related determinations (e.g., using a relationship between temperature and CRT variation to scale a CRT measurement or determination derived therefrom, using the temperature data to validate or reject a CRT measurement, or the like).

The device 100 can also include one or more motion sensors 204 to detect movement or motion of the device 100. The one or more sensors 204 can include a gyroscope, an accelerometer, the like, or combinations or multiples thereof. Movement or motion of the digit can affect CRT. Therefore, the motion data can optionally be used to indicate an error (e.g., when too much motion or movement occurs) or to account of blood flow variations due to the motion or movement.

The device 100 can also include a data processing module 208. One or more of the sensed data (e.g., force, light, temperature, motion) can be obtained as an analog signal. The data processing module 208 can convert the analog signal into a digital signal. The data processing module 208 can also process or analyze the sensed or converted data to obtain CRT determinations. The data processing module 208 can also receive and store the sensed or converted data.

The data processing module 208 can also filter, amplify, or filter and amplify one or more sensed data and can condition an output from the one or more sensors so the signals are represented by an analog voltage.

The device 100 also includes a network module 210 to transmit or receive communication to or from the intermediary device 220 or the control unit 230, such as via one or more connections.

In one example, the device 100 can be connected 240 to an intermediary device 220 which, in turn, is connected 242 to the control unit 230. The connection 240 can be a physical or wired connection, such as via universal serial bus (USB), a cable or wire, or can be wireless, such as via a wireless protocol. The wireless connection or protocol can be infrared, Bluetooth®, WiFi, Zigbee, or a combination thereof. The connection 240 allows communication between the device 100 and the intermediary device 220. Sensed data (e.g., force, light, temperature, motion) or processed data can be transmitted through the connection 240 to the intermediary device 220. The intermediary device 220 can then transmit the sensed or processed data to the control unit 230 via the connection 242, which can be physical or wired or wireless.

In another example, the device 100 can be connected 250 to the control unit 230. The connection, which can be physical or wired or wireless, 250 allows communication between the device 100 and the control unit 230. Sensed data (e.g., force, light, temperature, motion) or processed data can be transmitted through the connection 250 to the control unit 230.

The control unit 230 includes a data processing module 232 to process the data, calculate measurement quality, determine CRT result, the like, or combinations or multiples thereof. The control unit 230 also displays the results via an output 234 (e.g., display, screen, indicator, or the like), which can also include an output mechanism, such as a user interface 236 (e.g., GUI of a smartphone). In one example, the control unit 230 transmits data back to the device 100 or the intermediary device 220, e.g., for LED display. The LED display can indicate when a re-measurement is required and whether the measurement result is in an acceptable physiological range. The control unit 230 can then display or transmit the processed results, or portion thereof, to a user or practitioner. In one example, one or more functions of the control unit 230 can be implemented by the device 100.

The control unit 230 can also receive another physiological signal. The physiological signal correlates to a physiological or vital sign, including pulse rate, respiratory rate, blood pressure, blood oxygen levels, body temperature, the like, or combinations thereof.

The control unit 230 also includes a network module 238 to transmit or receive communication to or from the intermediary device 220, the control unit 230, or an external device, such as via one or more connections.

The CRT system 200 can also include an intermediary device 220, such as a wrist worn module, including one or more indicators 222 and a network module 224. The network module 224 transmits or receives communication to or from the device 100, the control unit 230, or an external device. The intermediary device 220 can include one or more indicators 222 (e.g., LEDs, screens, or the like), such as for data communication, feedback related to pressure application, CRT readings, errors, time, durations, alerts, notifications, the like, and combinations or multiples thereof. The one or more indicators 222 can also be used for a certain user population (e.g., LEDs that light up prior to and during measurement to distract pediatric patients). The intermediary device 220 can be worn by the patient, rested or located on a surface, held by another person, or the like. For example, the intermediary device 220 can include a strap formed of an elastic or flexible material including at least one of rubber, silicon rubber, hook-and-loop fastener, urethane resin, and plastic resin.

The intermediary device 220 can also include a data processing module 232 to process the data, calculate measurement quality, determine a CRT result, the like, or combinations or multiples thereof.

The device 100 and the intermediary device 220 can form a single, integrated wearable unit 260.

The data can be processed to include additional data or can be can processed to apply to additional conditions or determined, such as producing pulse oximetry data, to make additional clinical estimations or recommendations (e.g., dehydration, sepsis, or the like).

Figure 3:
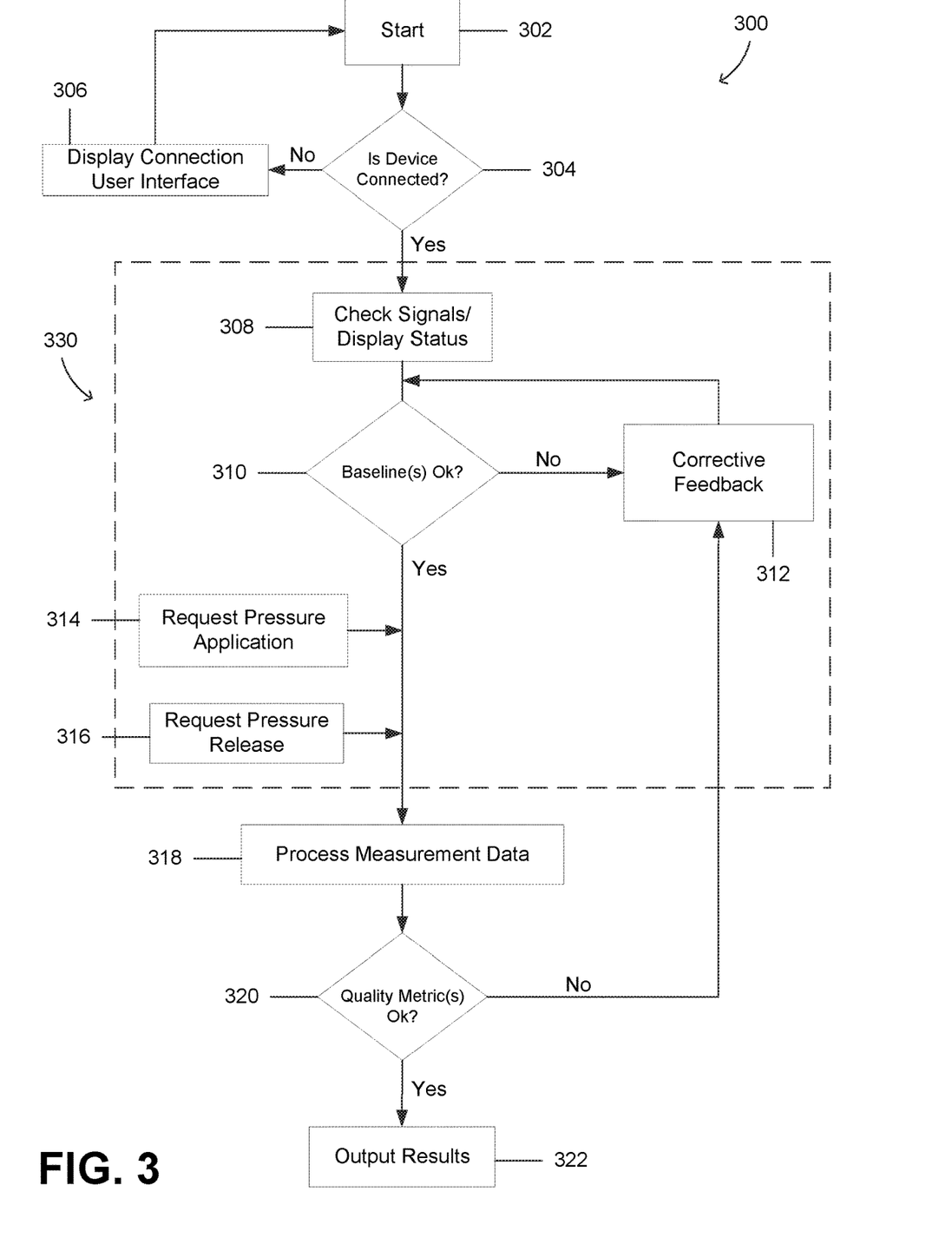
FIG. 3 is a flowchart of an example method.

FIG. 3 shows a flowchart of a method 300 for testing or data collection. At 302, the device 100 is turned on or the method is started. At 302, it is determined whether or not the device 100 is connected to the control unit 230. For ease of description and convenience, the control unit 230 is smartphone running a CRT application. However, the control unit 230 is not intended to be so limited. For example, the control unit 230 can be a computer, a tablet, a laptop, a patient monitor (e.g., a hospital monitor), or the like. If the device 100 is not connected to the control unit 230, at 306, a connection user interface is displayed to assist the user with establishing the connection, such as via Bluetooth pairing or selecting a device for connecting. Furthermore, one or more control units can include one or more applications. For example, a smartphone of a practitioner performing the CRT test includes a CRT application. The smartphone application can include functionality for or output related to, without limitation, end user instructions, quality metrics, predictions, and linked information. A hospital monitor application can include functionality for or output related to, without limitation, raw data signals or traces, CRT time, predictions, and EMR linkage.

Once connected, at 308, one or more sensors are checked to determine baseline signal data provided by the device 100. At 310, it is determined whether or not the baseline signal data and corresponding baseline measurements are acceptable. The data, measurements, or both can be displayed in a device screen, for example, listing detected force, optical and temperature data as real-time or live feedback 330.

Figure 4:
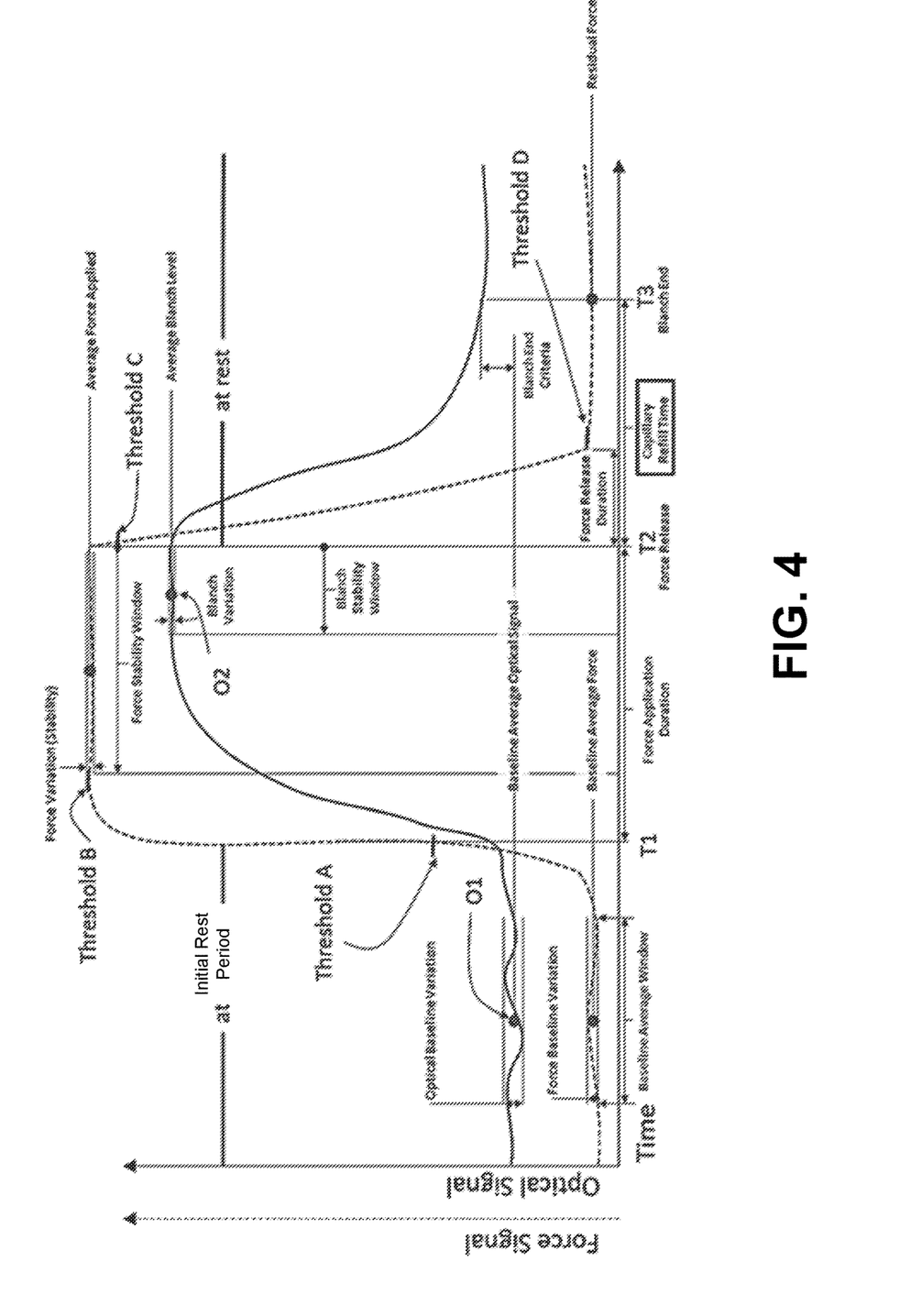
FIG. 4 is a plot of example data signals.

FIG. 4 shows a force data signal (dashed or broken line) and an optical data signal (solid line) resulting from the application and removal of the force.

In an initial rest period, the following data is collected by the optical sensor 124 and force sensor 134: optical signal changes prior to force application at T1 (a measurement of baseline optical stability or variation) and a force prior to T1 (a measure of baseline force stability or variation). The data is obtained to determine force and optical baselines. The data can also be obtained to ensure quality of measurement of CRT. For example, the force variation in the initial rest period is expected to be less than 0.5 Newtons (N). This level of variation is expected, as the device 100 is free-form. Furthermore, optical stability is expected to be in the range of +/−10% due to the blocking of ambient light by the strap 150 and overall device construction, even when the device is moved about.

Prior to T1, the force baseline is established. In one example, the force baseline is established by sampling force variation over time. A sliding window can be employed, whereby a window evaluates a first set of data falling within the window, and the window is then slid to a second set of data. The window has a width of a set length of time. The first and second sets of data can have at least one overlapping subset or individual piece of data, or the first and second sets of data can have no overlap. The window can have a width of 200-500 ms. As another example, the average force signal from a time prior to force application (e.g., 100-5000 ms prior to T1), can be stored for later processing use. Variation of the force signal within the baseline average can be calculated, such as by tracking the highest and lowest value of the force signal within the baseline averaging period (e.g., 100-5000 ms).

If any of the baseline data is found to be insufficient, corrective feedback, at 312, can be provided. For example, a force was not applied long enough, a temperature is too high or too low, too much movement or motion, or the like. Further details related to the corrective feedback may be given, for example information indicating that a longer pressure application is needed for force stabilization, achieving an adequate blanching period or blanching stabilization, or the like. This additional or different information can be desirable for different user populations (e.g., clinicians or other hospital personnel).

Feedback provided can include, without limitation, data indicating that a CRT test has or can begin, baseline measurements are obtained and are valid, an instruction to apply a force, a time or duration for which the force is to be applied (e.g., 3 seconds). The feedback can be visual, such as by visual indicators to provide real time or live feedback to demonstrate whether or the force application is at an adequate level, maintained for an adequate time, and that blanching has been achieved and maintained. Other live or real time feedback can be given, (e.g., an instruction to release the pressure at an appropriate time). Furthermore, alternative or additional data presentation formats can be utilized, including as traces or other graphics. Feedback can also display acceptable boundaries for force data, optical data, or both, which can be provided in real time or live feedback.

The operator feedback is provided to permit the operator to perform the test within desired or acceptable ranges or value. For example, when an operator is applying force the patient's finger, the operator feedback, whether in visual, audio, or optical format, can signal to the operator to increase or decrease pressure applied. The operator feedback can also be provided to signal to the operator to perform the next step in the test. For example, when the operator is applying force, operator feedback can be provided, whether in visual, audio, or optical format, to remove the pressure once desired blanching has been achieved.

User feedback can also be provided. User feedback can include a determination that the device is too tight or too loose, that the optical source or detector are not positioned properly on the patient, or finger temperature. The above conditions can affect CRT or collection of information for proper determination of CRT.

Post-event data can be provided to analyze where an error occurred so an operator can correct that action in subsequent tests. The post-event data can also be provided for training purposes or performance evaluation. For example, if an operator consistently applies too much pressure, the device may require, after 3 tries, that a new operator be used.

Returning to FIG. 3, if the baseline data is adequate, application of a force is request, at 314, and thereafter removal or release of the force is requested, at 316. In one example, the force is applied manually, such as by the practitioner.

At 318, data resulting from the application and remove of the force is measured and processed, including being analyzed by an algorithm. The data, such as that collected as discussed in FIG. 4, can be analyzed to obtain or determine one or more results.

At 320, quality metrics of the optical and force signals are checked, such as to confirm force and blanching stabilization, and acceptable force release duration. If the quality metrics are determined to be invalid, corrective feedback 312 can be provided. If the quality metrics are determined to be valid, results may be displayed, at 322.

Returning to FIG. 4, at time T1, a force is applied, such as via manual pressing on the patient's digit. The applied force is measured or sensed by the force sensor 134 (e.g., a force sensing resistor). The time from T1 to T2 represents a duration over which the force is applied. The force application duration is the detection of the applied force over a first threshold level (Threshold A). T1 indicates the start of the applied force and the beginning of capillary blanching. T2 indicates the time at which the applied force, having been removed or released, is reduced to Threshold C and the beginning of a CRT window.

The force signal is used to identify the time (T1) when the applied force reaches Threshold A. The force signal also used to identify the time (T2) when the applied force is removed or released and reaches Threshold C (i.e., the lower bound of the force stability window). During the time interval of T1 to T2, the force and optical signal characteristics are examined, such as with a sliding window, to determine measurement quality characteristics, including application of a sufficient or acceptable force level (i.e., achieving a force within the range of Threshold B and Threshold C) and the stability of force application (i.e., maintenance of the force within the threshold range for a sufficient duration). The sufficient or acceptable force level and the stability of force applicant provide acceptable blanching. In other words, the applied force should exceed a predetermined amount (e.g., Threshold C), and should be maintained within a range (between Thresholds B and C) for a period of time (i.e., the force stability window). Threshold C can be 50-99% of the average force within the force stability period, including 90%. The width of the force stability window can be 100 ms to 10 seconds (s), including 500 ms, 1 s, 3 s, or the like.

In one example, Threshold A is higher than the maximum value of the force variation in the initial rest period and lower than Threshold B, which is equal to the maximum force applied. Threshold C is lower than Threshold B and higher than Threshold A.

In one example, such as for teenager or adults, the applied force application can be in the range of 1.5-4.0 N. In another example, such as for children, toddlers, and babies, the applied force can be less than the applied for the adults or teenagers.

The force signal can be processed to determine the level of force application (e.g., directly via the device 100, the intermediary 220, the control unit 230, or combinations thereof), which can be reported as live or real-time feedback (e.g., via an LED or a user interface, such as an application or program). This aids the user or practitioner in applying the proper level of force to achieve blanching. This also aids the user or practitioner in avoiding patient discomfort.

Once a target range of force has been achieved, the force signal is further examined to determine stability. The force stability is the maintenance of a force within a threshold range for a sufficient duration. The force stability is determined by the variation (e.g., a value, a range or values, or a percentage) in applied force over a given period of time. In one example, force stability can vary by up to 20% (i.e., +/−20%) for a predetermined blanching period to achieve and maintain sufficient blanching for CRT measurement. In another example, the force stability period is to be maintained for up to twice as long as the blanching period. The blanching period can be up to 0.25 second, so that force stability period is up to 0.5 seconds. This allows for the optical signal to reflect blanch stability prior to force release. Any appropriate time period or duration can be used.

In another example, the duration is equal to or greater than 100 milliseconds (ms) and less than or equal to 5000 ms. A duration less than 100 ms does not provide a true snapshot of the force. A duration greater than 5000 ms is too long to properly evaluate a force. The threshold range can be a value or range of values that fall within a given range or percentage of an average of a maximum and a minimum of the baseline. For example, if a maximum is 1 N and a minimum is 0.5 N, the average is 0.75 N. The threshold range can be +/−10% of the average. So the force is considered stable if the calculated force within the sliding window falls within 0.575-0.650 N for a duration of 200 ms.

If the force applied during the time interval of T1 to T2 falls outside of a stable force value or range of stable force values for a given amount of time, then proper blanching has not been achieved and can lead to incorrect results or determinations. The test can therefore be run again. The user or practitioner can be notified accordingly.

The blanch stability can also be determined by a sliding window. In one example, the sliding window applied to blanching is narrower than (i.e., not as wide as) the window for the force baseline. For example, the window can be from 500-1000 ms.

The optical signal magnitude (i.e., amount) and stability are determined in the force application window (T1 to T2) to determine whether or not blanching has been achieved and maintained such that an accurate and reliable CRT measurement can be generated or obtained. The optical stability can be used to determine that blanching has stabilized and is suitable for use in measuring CRT. In one example, the optical signal is examined to determine when it has achieved a maximum. The optical variation in the optical signal during the force application window can also be determined. During the force stability window, the optical signal variation can be, for example, less than 10%, thereby indicating that blanching has stabilized. In another example, blanching can be analyzed as a comparison of received optical signal amount versus an expected amount or a previously received amount.

The optical signal during the initial rest period is obtained, such as by the optical sensor 124. O1 represents the average optical signal during the initial rest period. In other words, O1 represents a baseline value of the optical signal. For example, the average optical signal from a time prior to force application (e.g., 100-5000 ms prior to T1), can be stored for later processing use. Variation of the optical signal within the baseline average can be calculated, such as by tracking the highest and lowest value of the optical signal within the baseline averaging period (e.g., 100-5000 ms).

The optical signal during the force stability window is obtained, such as by the optical sensor 124. Stability of the optical signal during the force stability window is the blanch stability window (i.e., the blanch stability window can less than the force stability window). O2 represents the average optical signal during the blanch stability window. CRT is the time it takes for optical signal to return to O1 from O2 upon the release or removal of the applied force. In other words, a timing parameter is based on a characteristic of the force signal based on the applied force and on a characteristic of the optical signal based on the applied force. The applied force can also include the removal of the applied force. For example, the timing parameter includes the amplitude of the force signal that decreases to a CRT threshold at a point in time after removal of the force, and the amplitude of the optical signal, after removal of the force, that is equal to the baseline of the optical signal.

Failures in any measurement, including force application, can prompt an operator to perform the test again. The force application duration (T1-T2), optical signal changes prior to T1 (baseline optical stability), optical signal changes from T1 to T2 (blanch stability), force prior to T1 (baseline force), force changes following T1 (amount of force applied), force changes from T1 to T2 (force stability), force changes following T2 (duration of force release), and force following T2 (residual force) are processed to determine whether or not the signals or signal characteristics fall outside of a proper range, thereby rendering the CRT measurement invalid. For example, force release duration (beginning when the applied force is released or removed and the sensed force drops below Threshold C and ending when the sensed force transitions or meets Threshold D) that exceeds a predetermined amount of time can invalidate the CRT measurement. The residual force due to continued force application can extend the CRT, thereby invalidating the accuracy of the calculation or determination. As another example, insufficient force application or duration can lead to insufficient blanching, thereby reducing the CRT and invalidating the accuracy of the calculation or determination. As yet another example, a force applied during the T1-T2 time interval that falls outside of an accepted force range can affect the CRT due to increased blanching (e.g., force applied is greater than acceptable force application) or decreased blanching (e.g., force applied is less than acceptable force application). The CRT results obtained can be incorrect as the CRT will be less than expected due to decreased blanching or greater than expected due to increased blanching. As another example, improper force release duration can affect the CRT due to substantially the same reasons. A force release duration that is too slow will not trigger the capillary refill time while still permitting refilling to occur.

CRT signal assessment includes two force release times: initiation of force release and termination of force release. These values are used to calculate a force release duration. The CRT measurement can be invalid when the force release duration exceeds a desired duration. In one example, the force release duration is to be less than or equal to 100 ms, as this is 10-30 times less than typical capillary refill durations and therefore reflects a small comparative amount of time. In one example, the force duration release window can be utilized to adjust or shift the CRT, such as to account for a user or practitioner that has a longer force duration release.

In one example, the following table can include valid measurements for CRT calculations or determinations and can be determined by one or more processors using sensor signals.

| Characteristic | Valid Range | Notes |
| --- | --- | --- |
| T2-T1 | 2-5 seconds | |
| Baseline stability | +/−10% | Within a 3 second window |
| Blanch stability | +/−10% | |
| Baseline force | <0.5 Newtons | |
| Force applied | 1.5-4 Newtons | |
| Force stability | +/−20% | |
| Force release duration | <100 milliseconds | |
| Residual force | <0.5 Newtons | For a duration of 4 seconds after T2 |

In one example, Threshold D can equal the baseline force. In another example, Threshold D can be 1-50% of the average force of the force stability period.

It should be noted that although thresholds have been used to describe the process, the signal processing itself need not rely on static thresholds. Dynamic thresholds (e.g., threshold can be a percent deviation or can meet or exceed a given rate of change) can be employed, whereby the beginning and end of force application can be determined by determining an increase or decrease in the force signal that meets or exceeds a given or pre-determined rate of force signal change (i.e., slope). The rapidity and direction (increase or decrease) of force change can be determined by subtracting a value representing the current force with a force measured at a recent previous time. For example, subtracting a current sample of force from one or more past samples of force. As another example, optical thresholds (static or dynamic) can be employed to calculate the various optical metrics of interest.

The measurement quality is then calculated from an assessment of whether important measurement characteristics, such as those outlined in Table 1, are within desired ranges, and optionally, how close to optimal values the characteristics are. These metrics may be reported for review without further data (e.g., by a clinician), used to trigger a request for re-measurement (if suboptimal), or used to provide a validation (if measurement metrics are acceptable).

CRT is calculated as the time from force release (T2) to the time where the optical signal O2 returns to its baseline value O1 or within a predetermined range or percentage of the optical signal baseline. The return to the baseline value or within the pre-determined range or percentage is a blanch end criteria. The blanch end criteria can be calculated as a percentage of the difference between the average blanch level and the optical signal baseline O1. The blanch end criteria can be higher than the optical signal baseline O1. When the decreasing optical signal reaches a level matching the optical signal baseline O1 within this range, the optical signal is considered to have returned to baseline O1, with the patient's capillaries having been refilled to their baseline level, such as at time T3. Thus, the capillary refill time can be calculated as T3−T2, or alternatively, T3−T2−(Force Release Duration). The blanch end criteria can also be calculated by an algorithmic fit, such as an exponential decay curve, including an idealized curve. The blanch end criteria can also be calculated with a tracking or trending window, comparable to the sliding window. Though the width of the blanch end criteria window is 10 ms-1 s.

Mathematical models or algorithms can be applied to fit the signals to reduce a signal to noise ratio. Alternatively, one or more filters can be applied to the sensed data or data signals to reduce noise. The noise can be due to a heartbeat of the patient, mechanical factors, motion of the device 100, or the like. For example, an exponential decay signal model can be applied to the optical signal from T2 to T3. The model parameters can be adjusted until a minimum least squares error is reached. The model may then be used to calculate a refined blanch end time based on model projections of the optical signal's time to approach its baseline value.

The capillary refill timer starts when the force is released, as determined by the force sensor, and ends when the optical signal returns to a baseline value or falls within a range of the baseline value.

If the quality metrics are determined to be invalid, the CRT measurement process can be repeated. However, even if valid, the CRT measurement process can be repeated to establish an average CRT.

During the process, an application or program can display signal data and alerts, notifications, indications, or instructions regarding the steps to be performed. For example, a series of smartphone or tablet display updates can be provided. The application or program can also display information associated with the process or collection of data.

The displayed results may take a variety of forms. For example, a CRT measurement time, an averaged CRT, a scaled score or a related metric, including a color-coded output to indicate healthy CRT versus a CRT that indicates a condition.

The application or program can also link to clinical information or contact information, such as to guide the user, practitioner, or caregiver with next steps.

Though light reflection is discussed, light absorption or transmission can also be determined. Absorption is the inverse of transmission. In other words, a digit having increased light transmission (i.e., more light passes through the digit due to decreased external capillary bed blood flow) has a decreased light absorption (i.e., less light is absorbed when passed through the digit due to decreased external capillary bed blood flow). However, a digit having decreased light transmission (i.e., less light passes through the digit due to increased external capillary bed blood flow) has an increased light absorption (i.e., more light is absorbed when passed through the digit due to increased external capillary bed blood flow).

Though practitioner is discussed, any user is also contemplated, including an end user, an operator, a clinician, a parent, a caregiver, or the like.

Embodiments or examples of the invention can include a non-transitory computer readable medium which can store instructions for performing the above-described methods and any steps thereof, including any combinations of the same. For example, the non-transitory computer readable medium can store instructions for execution by one or more processors or similar devices.

Further embodiments or examples of the present invention can also include the one or more user equipment(s), network sites, backend network, or servers which read out and execute computer executable instructions, such as a non-transitory computer-readable medium, recorded or stored on a storage medium (which may be the same as or different than the storage medium for storing images or files, as discussed above), to perform the functions.

For example, non-transitory computer readable medium can store instructions for execution by one or more processors or similar devices to perform the method of data collection. As another example, non-transitory computer readable medium can store instructions for execution by one or more processors or similar devices to perform data analysis, including CRT calculation and analysis, feedback, quality metric analysis, alerts, notifications, indications, condition determination, treatment determination, the like, or combinations or multiples thereof.

Though certain elements, aspects, components or the like are described in relation to one embodiment or example, such as an example capillary refill timing system, those elements, aspects, components or the like can be including with any other capillary refill timing systems, such as when it desirous or advantageous to do so.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

What is claimed is:

1. A device for measuring a capillary refill time (CRT), comprising:
    a wearable component comprising:
        a force sensor configured to generate a force signal representative of a force applied to a digit of a patient over time, and
        an optical sensor configured to generate an optical signal representative of optical energy received from an optical source over time; and
    a processor programmed to:
        determine a timing parameter of the applied force within a force duration window, the timing parameter based on a characteristic of the force signal and a characteristic of the optical signal,
        calculate the CRT based on the timing parameter, and
        output a value of or data related to the CRT.

2. The device of claim 1, wherein the wearable component further comprises the optical source configured to emit the optical energy.

3. The device of claim 1, wherein the optical source is external to the wearable component.

4. The device of claim 1, wherein the processor is further programmed to receive at least one other physiological signal.

5. The device of claim 1, wherein the processor is further programmed to output the value of the CRT or data relating to the CRT to a user.

6. The device of claim 5, wherein the value of or the data relating to the CRT identifies a patient condition, an error when the applied force exceeds an applied force threshold or falls outside of an applied force threshold range, or a time duration.

7. The device of claim 1, further comprising an intermediary device communicatively coupled to the wearable component.

8. The device of claim 7, wherein the wearable component further comprises a communication module to transmit the force and optical signals to the intermediary device via wired or wireless connection.

9. The device of claim 7, wherein the intermediary device comprises a data processing module programmed to convert sensed data from an analog signal to converted data.

10. The device of claim 9, wherein the converted data is a digital signal, force sensor data, optical sensor data, a quality measurement, or a CRT result.

11. The device of claim 1, wherein the characteristic of the force signal is an amplitude of the force signal at a time after removal of the force applied to the digit.

12. The device of claim 11, wherein the force is applied manually.

13. The device of claim 1, wherein the characteristic of the optical signal is an amplitude of the optical signal at a time after removal of the force applied to the digit.

14. The device of claim 13, wherein the force is applied manually.

15. The device of claim 1, wherein the force characteristic is an amplitude of the force signal at a point in time when the amplitude of the force signal decreases to a CRT threshold, and wherein the optical signal characteristic is an amplitude of the optical signal at a point in time when the amplitude of the optical signal is equal to a baseline amplitude of the optical signal.

16. A method for determining a capillary refill time (CRT), the method comprising:
    receiving a force signal representative of a force applied manually to a digit of a patient over time;
    receiving an optical signal representative of optical energy received from an optical source over time;
    determining a timing parameter of the applied force within a force duration release window, the timing parameter based on a characteristic of the force signal and a characteristic of the optical signal;
    calculating the CRT based on the timing parameter; and
    generating an instruction to output a value of or data related to the CRT.

17. The method of claim 16, further comprising determining a patient condition based on the CRT.

18. The method of claim 16, further comprising outputting a value or data related to the CRT, an alert, or a notification.

19. A non-transitory computer readable medium for calculating a capillary refill time (CRT), comprising machine-readable instructions that, when executed on one or more processors, perform one or more operations comprising:
    acquiring a force signal representative of a force applied manually to a digit of a patient over time;
    receiving an optical signal representative of optical energy received from an optical source over time;

determining a timing parameter of the applied force within a force duration release window, the timing parameter based on a characteristic of the force signal and a characteristic of the optical signal;
calculating the CRT based on the timing parameter; and
generating an instruction to output a value of or data related to the CRT.

20. The non-transitory computer readable medium of claim 19, wherein the one or more operations further comprises outputting the value of or the data related to the CRT, an alert, or a notification.

\* \* \* \* \*

UNITED STATES PATENT AND TRADEMARK OFFICE
CERTIFICATE OF CORRECTION

| | | |
|---|---|---|
| PATENT NO. | : 11,806,114 B2 | Page 1 of 1 |
| APPLICATION NO. | : 16/887846 | |
| DATED | : November 7, 2023 | |
| INVENTOR(S) | : David Sheridan et al. | |

It is certified that error appears in the above-identified patent and that said Letters Patent is hereby corrected as shown below:

In the Specification

On Column 1, Line 3, before the "BACKGROUND OF THE INVENTION", please insert the following paragraph:
-- STATEMENT REGARDING FEDERALLY SPONSORED RESEARCH OR DEVELOPMENT
This invention was made with government support under TR002369 awarded by the National Institutes of Health. The government has certain rights in the invention. --

Signed and Sealed this
Fifth Day of November, 2024

Katherine Kelly Vidal
*Director of the United States Patent and Trademark Office*